(12) United States Patent
Linn et al.

(10) Patent No.: US 7,256,577 B2
(45) Date of Patent: Aug. 14, 2007

(54) HIGH FREQUENCY ROTARY EDDY CURRENT PROBE DEVICE

(75) Inventors: John R. Linn, Maple Valley, WA (US); Joseph F. Floyd, Up, WA (US)

(73) Assignee: The Boeing Company, Chicago, IL (US)

( * ) Notice: Subject to any disclaimer, the term of this patent is extended or adjusted under 35 U.S.C. 154(b) by 252 days.

(21) Appl. No.: 11/102,178

(22) Filed: Apr. 7, 2005

(65) Prior Publication Data

US 2006/0226834 A1    Oct. 12, 2006

(51) Int. Cl.
    *G01R 33/14*      (2006.01)
    *G01N 27/90*      (2006.01)

(52) U.S. Cl. .................. 324/240; 324/222; 324/241; 324/242

(58) Field of Classification Search ................ 324/222, 324/223, 228, 234, 236–243
See application file for complete search history.

(56) References Cited

U.S. PATENT DOCUMENTS

| | | | |
|---|---|---|---|
| 3,617,874 A * | 11/1971 | Forster | ........................ 324/241 |
| 3,963,980 A | 6/1976 | Shkarlet | |
| 4,706,020 A | 11/1987 | Viertl et al. | |
| 5,481,916 A | 1/1996 | Macecek et al. | |
| 5,689,183 A * | 11/1997 | Kohama | ........................ 324/233 |
| 5,691,687 A | 11/1997 | Kumagai et al. | |
| 5,701,073 A * | 12/1997 | Baker | ........................ 324/117 H |
| 6,377,040 B1 * | 4/2002 | Hell | ........................ 324/240 |

FOREIGN PATENT DOCUMENTS

| | | |
|---|---|---|
| EP | 0669530 A1 | 8/1995 |
| EP | 0924516 A2 | 6/1999 |
| GB | 2273782 A | 6/1994 |
| WO | WO99/28739 | 6/1999 |

OTHER PUBLICATIONS

Basic Principles of Eddy Current Inspection, retrieved from http://www.ndt-ed.org/EducationResources/CommunityCollege/Eddy/Currents/Introduction/IntroductiontoET.htm, Mar. 8, 2005.

* cited by examiner

*Primary Examiner*—Edward Lefkowitz
*Assistant Examiner*—Kenneth J Whittington
(74) *Attorney, Agent, or Firm*—Ingrassia Fisher & Lorenz, P.C.

(57) ABSTRACT

An eddy current detection system configured in accordance with an example embodiment of the invention employs a high frequency rotary eddy current probe that is capable of detecting very shallow surface imperfections, including imperfections originating at scribe lines located near lap joints on an aircraft fuselage. The rotary eddy current probe includes a differential sensing coil arrangement surrounded by a reflection coil, both of which are located within the probe tip housing of the rotary eddy current probe. The differential sensing coil arrangement and the reflection coil are positioned off-axis within the rotary eddy current probe. In addition, the rotary eddy current probe employs a partial electromagnetic shield that does not completely surround the differential sensing coil arrangement.

21 Claims, 8 Drawing Sheets

HIGH FREQUENCY ROTARY EDDY CURRENT PROBE DEVICE

TECHNICAL FIELD

The present invention relates generally to eddy current test equipment for inspection of shallow cracks in the surface of a component. More particularly, the present invention relates to a high frequency eddy current test probe design.

BACKGROUND

Lap joints are created when two or more aircraft skin panels are joined, and a portion of one panel (e.g., an inner panel) is overlapped by portion of another panel (e.g., an outer skin panel). The term "lap joint," as used herein, refers both to longitudinal joints, as formed when outer (e.g., an upper longitudinal panel) and inner (e.g., a lower longitudinal panel) fuselage skin panels are joined, and to circumferential or butt joints, as formed when two curved skin panel assemblies are joined by a structural panel (e.g., a splice plate). Similarly, the term "inner panel," as used herein, may refer to any structural panel (e.g., a splice plate or an inner fuselage skin panel) that is at least partially overlapped at a lap joint. Lap joint panels are typically joined together utilizing an anti-corrosive sealant and rows of rivets disposed proximate the overlapping edge of the outer skin panel.

It has been discovered that the surface of inner panels may be scratched proximate the lap joints during routine maintenance. For example, very fine and shallow scribe lines may be created by certain tools during removal of excess lap joint sealant. The scribe lines may be blended out by abrasively removing a shallow volume of material along the surface of the panel, providing that scratches are visible and accessible and that the scratched skin panel is sufficiently thick. Alternatively, it may be necessary to remove a portion of the panel and install and install a replacement panel such as a repair doubler. In any event, the detection of scribe lines and other surface imperfections can be an important aspect of aircraft maintenance.

For practical maintenance cost reasons, it should be possible to detect scribe lines and other surface imperfections of aircrafts panel in a non-laboratory environment. Traditional detection techniques include visual inspection and the use of low and high frequency eddy current inspection equipment. In practice, however, the fuselage skin of an aircraft usually has surface irregularities that can mask the test signals generated by conventional eddy current inspection technologies. In addition, conventional eddy current inspection technologies may not be sensitive enough to detect extremely shallow imperfections. In this regard, typical high frequency eddy current detection systems can detect surface irregularities that are at least 0.020 inch deep. Such conventional systems are not suitable for the detection of the fine scribe line and cracks described above, which can be as shallow as 0.003 inch deep.

Accordingly, it is desirable to have a system for rapidly detecting very shallow imperfections in the fuselage skin of an aircraft in a manner that is immune to normal or acceptable surface irregularities. In addition, it is desirable to have a field-deployable eddy current detection system that is sensitive enough to detect very shallow irregularities that would otherwise remain undetected by conventional eddy current systems. Furthermore, other desirable features and characteristics of the present invention will become apparent from the subsequent detailed description and the appended claims, taken in conjunction with the accompanying drawings and the foregoing technical field and background.

BRIEF SUMMARY

An eddy current crack detection apparatus is provided for detecting shallow cracks in the surface of a structure such as an aircraft fuselage. The apparatus is suitable for crack detection in the vicinity of lap joints. The apparatus is capable of quickly and accurately detecting extremely shallow cracks using a high frequency test signal.

The above and other aspects of the invention may be carried out in one form by a high frequency eddy current probe configured as described herein. The high frequency eddy current probe includes a probe tip housing having an interior, a perimeter, and a rotating axis, a differential sensing coil arrangement located within the interior in a position offset from the rotating axis and biased toward the perimeter, and a partial electromagnetic shield coupled to the probe tip housing and positioned such that the differential sensing coil arrangement is located between the partial electromagnetic shield and the rotating axis. The partial electromagnetic shield spans only a portion of the perimeter.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the invention or the application and uses of the invention. For example, those skilled in the art will appreciate that the present invention may be practiced in conjunction with the testing of any structure or surface and that the aircraft lap joint testing system described herein is merely one exemplary application for the invention. Furthermore, there is no intention to be bound by any expressed or implied theory presented in the preceding technical field, background, brief summary or the following detailed description.

For the sake of brevity, conventional techniques related to eddy current testing, the generation, collection, and analysis of eddy current test signals, inductive coil design, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

As used herein, a "node" means any internal or external reference point, connection point, junction, signal line, conductive element, or the like, at which a given signal, logic level, voltage, data pattern, current, or quantity is present. Furthermore, two or more nodes may be realized by one physical element (and two or more signals can be multiplexed, modulated, or otherwise distinguished even though received or output at a common mode).

Figure 6:
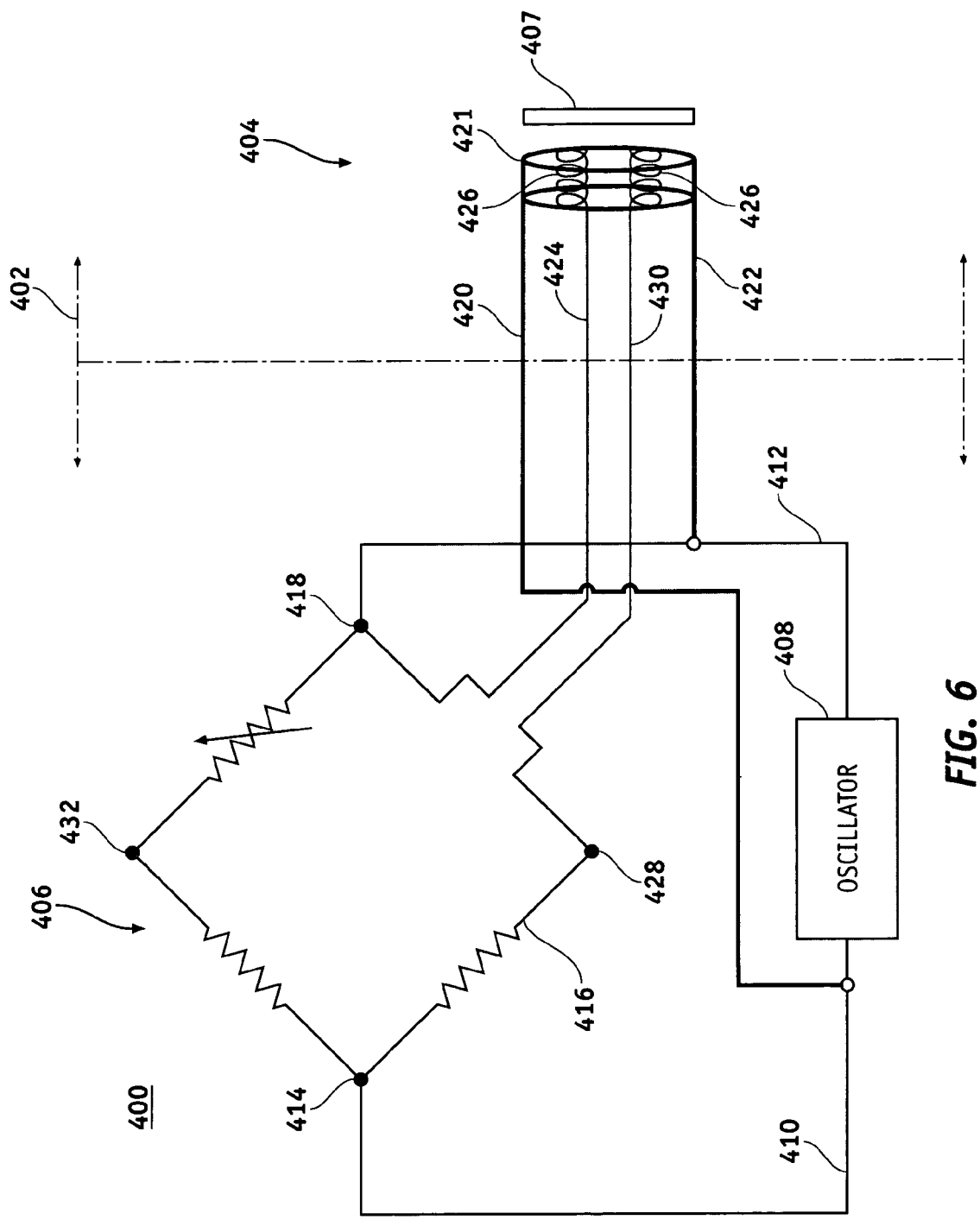
FIG. 6 is a schematic circuit diagram of an eddy current crack detection system configured in accordance with an example embodiment of the invention.

The following description refers to nodes or features being "connected" or "coupled" together. As used herein, unless expressly stated otherwise, "connected" means that one node/feature is directly or indirectly connected to another node/feature, and not necessarily mechanically or physically. Likewise, unless expressly stated otherwise, "coupled" means that one node/feature is directly or indirectly coupled to another node/feature, and not necessarily mechanically or physically. Thus, for example, although the schematic shown in FIG. 6 depicts one example arrangement of elements, additional intervening elements, devices, features, or components may be present in an actual embodiment (assuming that the functionality of the circuit is not adversely affected).

As mentioned above, surface irregularities (which, for example, may be present on the fuselage skin of an aircraft) can mask test signals from traditional high frequency eddy current inspection systems. The eddy current crack detection system described herein, however, is not masked by such surface irregularities. Consequently, the system described herein is capable of detecting cracks as shallow as 0.003 inch, while existing technologies are typically limited to the detection of cracks as shallow as 0.020 inch. It should be appreciated that the invention described herein can be utilized to inspect any suitable surface, and that the inspection of an aircraft fuselage and lap joints as described herein are merely example applications of the invention.

Briefly, a crack detection system configured in accordance with a practical embodiment of the invention employs eddy current inspection techniques to detect very shallow cracks in the surface of a test part. The crack detection system utilizes a high frequency rotary eddy current probe having two cylindrical eddy current sensing coils placed in close proximity to each other to reduce the effects of surface irregularities such as aluminum clad layer thinning, which may be present in an aircraft fuselage. The sensing coils are shielded with an electromagnetic shield that does not completely surround the sensing coil arrangement. The sensing coils are arranged in a differential configuration and connected to a bridge circuit such that no net change is detected when both sensing coils detect the same impedance variation (such a condition would be found in areas where clad layer thinning is present). If, however, the high frequency rotary eddy current probe is scanned over a crack, only one of the two sensing coils instantaneously detects the crack and a net difference in the impedance is registered as a crack signal. To further enhance the crack detection capability of the system, the sensing coil arrangement is mounted in an offset fashion within the probe such that the sensing coils trace a circular pattern in response to rotation of the probe. A fixed rotational speed of the probe results in a constant scan rate, which is desirable to enable filtering of unwanted frequencies caused by surface irregularities such as dents, gouges, clad layer thinning, and probe wobble.

Figure 1:
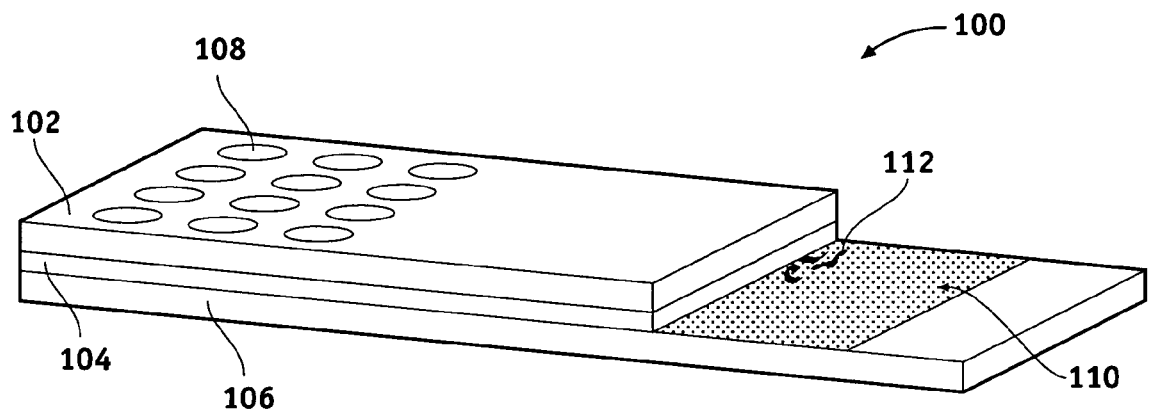
FIG. 1 is a perspective view of an untrimmed longitudinal lap joint.
Figure 2:
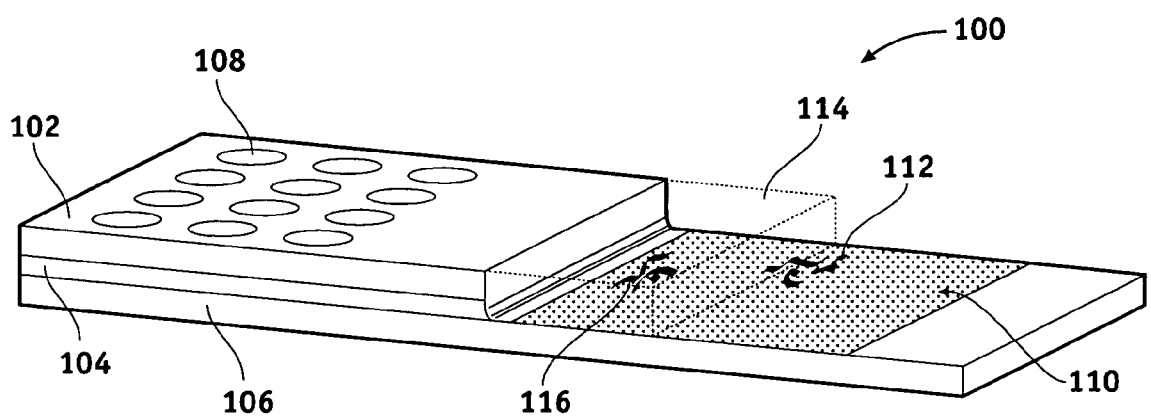
FIG. 2 is a perspective view of the longitudinal lap joint of FIG. 1, after trimming.

FIG. 1 is a perspective view of an untrimmed longitudinal lap joint 100, such as that typically found on an aircraft fuselage, and FIG. 2 is a perspective view of lap joint 100 after trimming. Longitudinal lap joints typically join an outer fuselage skin panel to an inner overlapped fuselage skin panel. Lap joint 100 includes an outer skin panel 102, a doubler 104, and an inner skin panel 106. Outer skin panel 102 may be bonded by way of an anti-corrosion sealant (not shown in FIG. 1 or FIG. 2) to doubler 104, and doubler 104 may be bonded by way of anti-corrosion sealant (not shown) to inner skin panel 106. Each of these three layers is further coupled together by a plurality of rivets 108 (e.g., three rows of counter-sunk rivets). Outer skin panel 102, doubler 104, and inner skin panel 106 may be manufactured from a lightweight material (e.g., aluminum) and may have a base metal component comprising an alloy (e.g., aluminum-copper).

An area 110 (shown exaggerated for clarity) of the outer surface of inner panel 106 is prone to scratching during aircraft maintenance (e.g., during removal of excess sealant). Area 110 is disposed proximate the overlapping edge of lap joint 100 and roughly corresponds to the location of excess sealant that may have been removed during maintenance. When lap joint 100 is untrimmed as shown in FIG. 1, only a portion of area 110 may be seen. After lap joint 100 is trimmed as shown in FIG. 2, however, area 110 may be seen in its entirety.

A series of scratches 112 (e.g., scribe marks made, perhaps, by a cutting tool used to remove excess sealant) is present on inner skin panel 106 within area 110. Prior to trimming (see FIG. 1), scratches 112 may only be partially visible. After trimming (see FIG. 2), however, scratches 112 are entirely visible. The presence of scratches 112 suggests that inner skin panel 106 may have additional scratches within or proximate area 110 that are hidden by an overlapping edge 114 of outer skin panel 102 and doubler 104. Edge 114 may be trimmed (i.e., removed) without weakening lap joint 100 to reveal area 110 in its entirety and thus permit further inspection thereof. As can be seen in FIG. 2, trimming of edge 114 reveals a second series of scratches 116 that was hidden by edge 114 prior to trimming.

Figure 3:
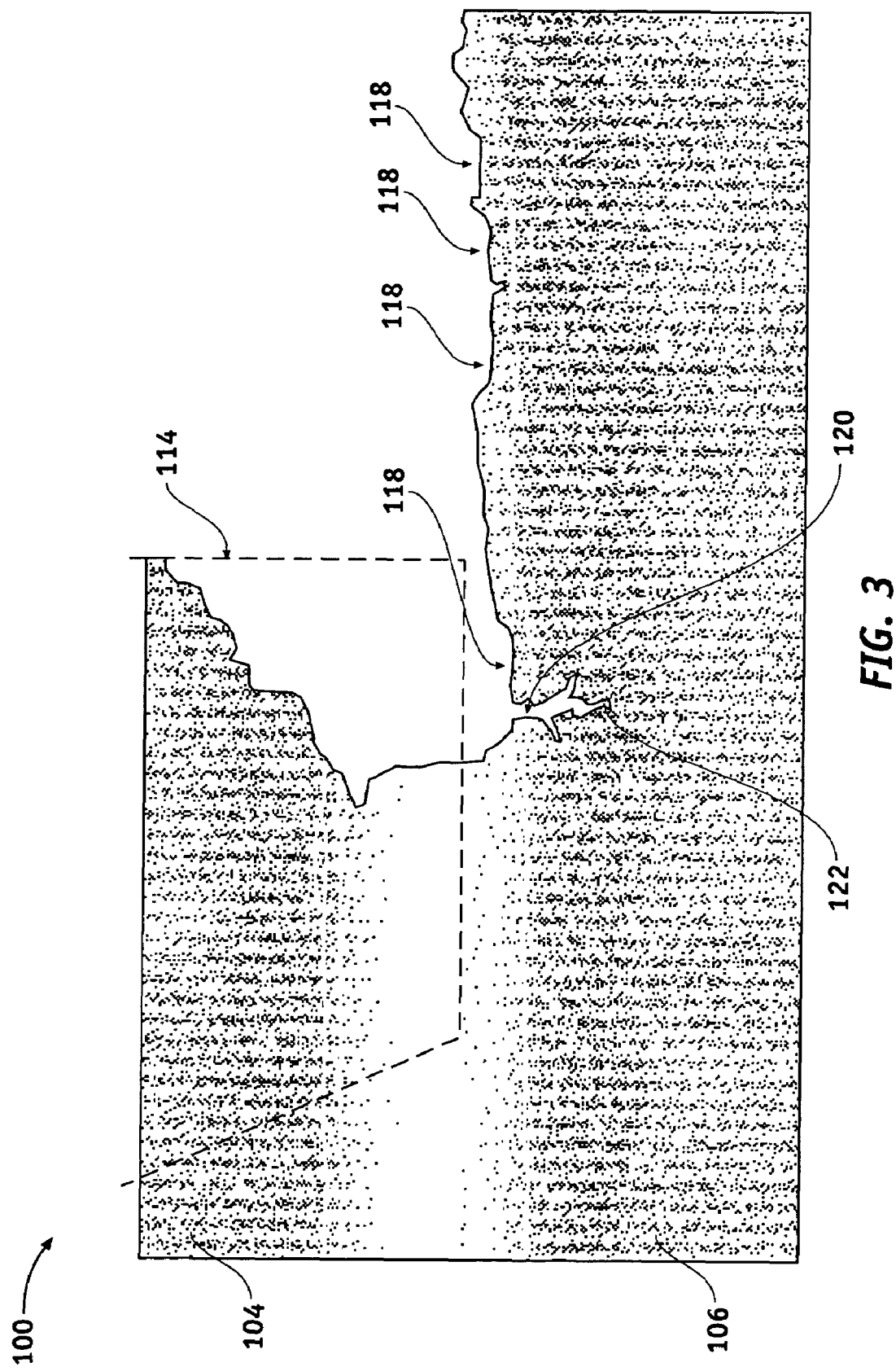
FIG. 3 is a magnified photographic cross-sectional view of the untrimmed lap joint shown in FIG. 2.

FIG. 3 is a magnified photographic cross-sectional view of untrimmed lap joint 100 shown in FIG. 2. As can be seen, a plurality of scratches 118 including a scratch 120 is present on the outer surface of inner skin panel 106. An imperfection 122 has initiated from scratch 120 and extends downward into inner skin panel 106. When lap joint 100 is untrimmed (FIG. 1), scratch 120 is hidden from view by overlapping edge 114. Trimming of edge 114, however, may reveal scratch 120. In practice, trimming of edge 114 may be accomplished by the means of a suitable trim tool that removes edge 114 away from outer skin panel 102 and doubler 104. It is desirable that the trim tool removes most or all of edge 114 while leaving inner skin panel 106 unscathed. Generally, the trim tool should be of the type capable of trimming 0.070 plus or minus 0.010 inch.

After edge 114 has been trimmed away from lap joint 100, the newly exposed section of inner skin panel 106 including area 110 may be examined for scratches and cracks. Scratches may be detected by, for example, visual observation. Cracks, which may extend further below the surface of inner skin panel 106, may be detected using the HFEC crack detection system described in more detail below.

Figure 4:
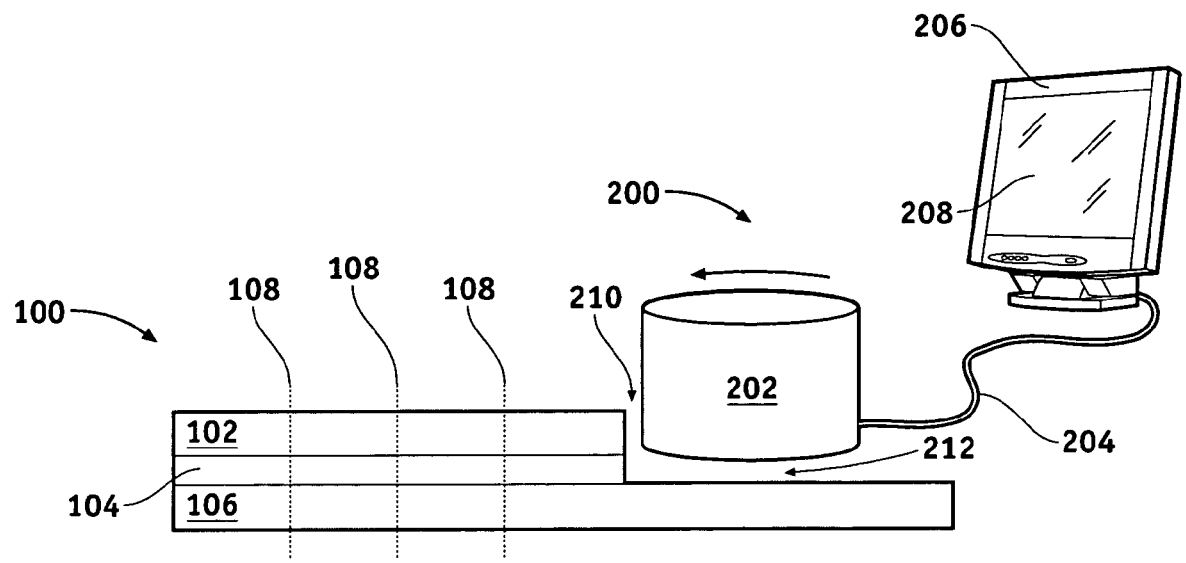
FIG. 4 is diagram of a lap joint under test and a high frequency eddy current ("HFEC") crack detection system.

An example HFEC crack detection system 200 is illustrated in FIG. 4. HFEC crack detection system 200 includes a rotating probe 202 coupled by way of a connector cable 204 to an inspection instrument 206 having a display 208. The curved arrow above rotating probe 202 represents the direction of rotation relative to lap joint 100. In a practical embodiment of the invention, HFEC crack detection system 200 is suitably configured such that rotating probe 202 is held away from the trimmed edge of lap joint 100 and above the surface under inspection. In this regard, FIG. 4 depicts a gap 210 between rotating probe 202 and lap joint 100 and a gap 212 between rotating probe and inner skin panel 106. Gap 210 is maintained to ensure that rotary probe 202 detects scribe lines and cracks in the target vicinity of lap joint 100. In the example embodiment, gap 210 is approximately 0.020 (±0.005) inch wide, and gap 212 is approximately 0.005 (±0.003) inch high. These gaps are maintained by the particular design of the rotary probe assembly and rotary mount assembly as described herein.

Figure 5:
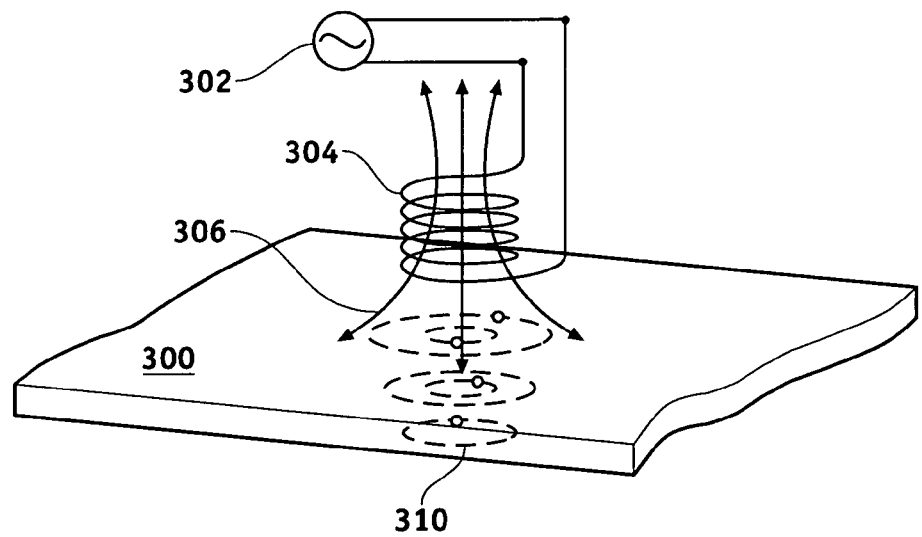
FIG. 5 is a schematic representation of the generation of eddy currents in a test article by an HFEC crack detection system of the type shown in FIG. 4.

As illustrated in FIG. 5, HFEC crack detection system 200 creates eddy currents within an article 300 (e.g., a structural panel such as inner skin panel 106) by delivering an alternating current signal 302 via a plurality of conductive coils 304 associated with rotating probe 202. Alternating current signal 302 induces an alternating magnetic field 306 in article 300, which causes eddy currents 310 to flow within article 300. The strength of eddy currents 310 are measured by probe 202 and a graphical representation of characteristics of eddy currents 310 is displayed on display 208. If the observed conductivity is significantly below a predicted value, current-impeding cracks are likely present in the tested article 300 and crack repair or other appropriate measures may be undertaken.

FIG. 6 is a schematic circuit diagram of an eddy current crack detection system 400 configured in accordance with an example embodiment of the invention. The portion to the right side of dashed line 402 represents a high frequency rotary eddy current probe 404, while the portion to the left side of dashed line 402 represents an eddy current instrument 406 configured to generate test signals, receive test signals, and process the received test signals. Crack detection system 400 may be utilized to scan for cracks in the surface of a test part 407.

Eddy current instrument 406 may include an oscillator 408 or other suitable test signal generator that operates in a conventional manner to generate an alternating current test signal for system 400. As depicted in FIG. 6, oscillator 408 applies the test signal to a first node 410 and a second node 412. First node 410 is coupled to a first input 414 of a bridge circuit 416, and second node 412 is coupled to a second input 418 of bridge circuit 416. In this example embodiment, first node 410 corresponds to first input 414 and second node 412 corresponds to second input 418. First node 410 is also coupled to a first lead 420 of a reflection coil 421, and second node 412 is also coupled to a second lead 422 of reflection coil 421. In this practical embodiment, first node 410 corresponds to first lead 420 and second node 412 corresponds to second lead 422. Second input 418 of bridge circuit 416 is also coupled to a first lead 424 of a differential sensing coil arrangement 426, and a third input 428 of bridge circuit 416 is coupled to a second lead 430 of differential sensing coil arrangement 426. In the illustrated embodiment, second input 418 of bridge circuit 416 corresponds to first lead 424 of differential sensing coil arrangement 426, and third input 428 of bridge circuit 416 corresponds to second lead 430 of differential sensing coil arrangement 426.

Although not depicted in FIG. 6, eddy current crack detection system 400 includes a suitable test signal connector between high frequency eddy current probe 404 and eddy current instrument 406. The test signal connector is coupled to reflection coil 421 and to differential sensing coil arrangement 426, and is configured to provide the alternating current test signal to reflection coil 421. This connector allows probe 404 to rotate while maintaining electrical connectivity for leads 420, 422, 424, and 430. In operation, oscillator 408 generates a suitable alternating current test signal and applies the test signal to reflection coil 421. In accordance with one example embodiment of the invention, the test signal has a frequency between 100 kHz and 3.0 MHz. The test signal creates eddy currents in test part 407, and those eddy currents are sensed by differential sensing coil arrangement 426. Bridge circuit 416, which is connected to differential sensing coil arrangement 426 as described above, functions in a conventional manner to process the signals sensed by differential sensing coil arrangement 426. For example, a suitable detector or monitor (not shown) may be coupled between third input 428 of bridge circuit 416 and a fourth input 432 of bridge circuit 416 to obtain a diagnostic signal that is representative of the condition of the surface of test part 407. In this regard, the diagnostic signal may have characteristics indicative of the presence (or absence) of cracks in the surface of test part 407, and/or characteristics indicative of the depth of cracks in the surface of test part 407.

Figure 7:
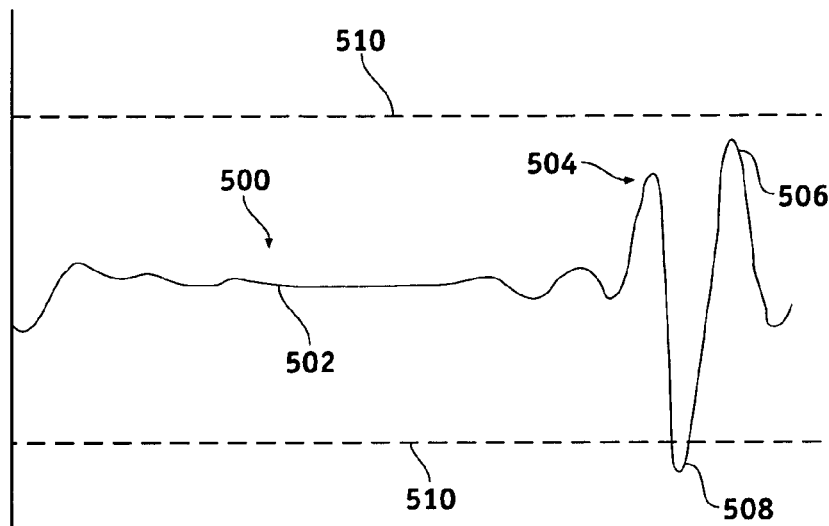
FIG. 7 is a graph of an example diagnostic signal, which may be generated by an eddy current crack detection system configured in accordance with an example embodiment of the invention.

FIG. 7 is a graph of an example diagnostic signal 500, which may be generated by eddy current crack detection system 400. Referring to FIG. 4, diagnostic signals such as signal 500 may be generated and displayed on display 208 of inspection instrument 206. The horizontal scale represents the lateral position of the eddy current probe on the test part, and the vertical scale represents crack depth. The relatively flat portion 502 of diagnostic signal 500 indicates an absence of measurable cracks, while the relatively dynamic portion 504 of diagnostic signal 500 indicates the presence of a measurable crack. A positive peak 506 represents the detection of the crack by a first sensing coil, and a negative peak 508 represents the detection of the crack by a second sensing coil. The vertical scale of the display may include gradations 510 that represent a predetermined crack depth threshold.

Figure 8:
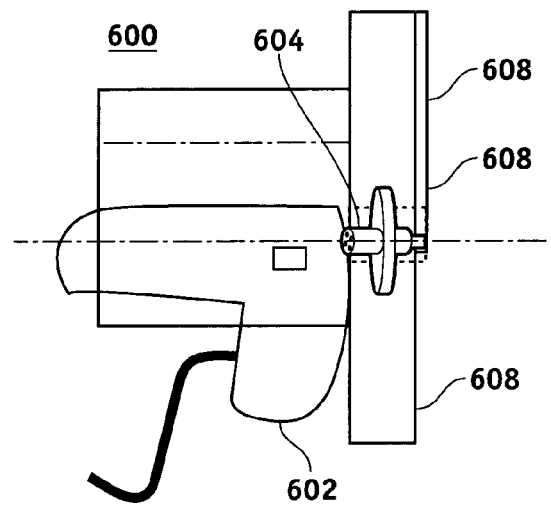
FIG. 8 is a side phantom view of an eddy current crack detection device configured in accordance with an example embodiment of the invention.

In practical embodiments of the invention, the high frequency rotary eddy current probe is mounted to a suitably configured rotary drive, forming an eddy current crack detection device. The device, in turn, is coupled to the eddy current instrument via a suitable cable or other electrical connection (which may be wired or wireless). FIG. 8 is a side phantom view of an eddy current crack detection device 600 configured in accordance with an example embodiment of the invention. Device 600 generally includes a rotary drive 602, a high frequency eddy current probe 604 coupled to rotary drive 602, and a rotary mount 606 coupled to rotary drive 602 and to probe 604. Rotary drive 602 is configured to rotate probe 604 during scanning of the test part. In accordance with one practical embodiment of the invention, rotary drive 602 rotates probe 604 at a speed between 100 and 3000 RPM; the exact rotational speed may vary from one application to another. For any given scan, rotary drive 602 maintains the rotational speed constant. Rotary mount 606 is suitably configured to stabilize probe 604 while rotary drive 602 rotates probe 604. More specifically, rotary mount 606 stabilizes the probe tip housing (described below) of probe 604 to reduce probe wobble and related noise in the system.

In practice, high frequency eddy current probe 604 is physically and electrically coupled to rotary drive 602. In turn, rotary drive 602 is coupled to rotary mount 606 to form a handheld eddy current crack detection device 600 that can be passed over the surface of the test part while rotary drive 602 spins probe 604 within rotary mount 606. In this example embodiment, rotary mount 606 includes a stepped contact surface 608 to accommodate testing of lap joints (the step serves as a guide that follows the lap joint edge during testing). As described in more detail below, rotary mount 606 includes a bearing arrangement that allows probe 604 to rotate freely within rotary mount 606 in a stable manner with little or no probe wobble. Furthermore, rotary mount 606 is designed such that the end surface of probe 604 is maintained at a controlled height above the surface of the test part, e.g., 0.005 (±0.003) inch above the test part in one practical embodiment. This height may be more or less, depending upon the specific application for the probe.

Figure 9:
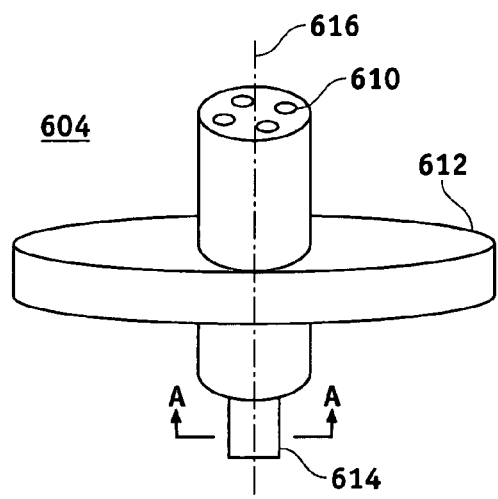
FIG. 9 is a perspective view of a high frequency eddy current probe configured in accordance with an example embodiment of the invention.

FIG. 9 is a perspective view of high frequency eddy current probe 604. It should be appreciated that, in a practical deployment, the specific size, shape, and configuration of probe 604 may vary from that shown in FIG. 9. Probe 604 generally includes an electrical connector 610, a flange 612, and a probe tip housing 614 coupled to flange 612. Probe 604 includes a rotating axis 616 which preferably corresponds to the central longitudinal axis of probe 604, as depicted in FIG. 9. Although not shown in FIG. 9, probe tip housing 614 contains a reflection coil and a differential sensing coil arrangement (described in more detail below). Electrical connector 610 establishes the electrical lead connections necessary for the reflection coil and the differential sensing coil arrangement, and the leads are routed within probe 604 between electrical connector 610 and probe tip housing 614 in an appropriate manner.

Figure 10:
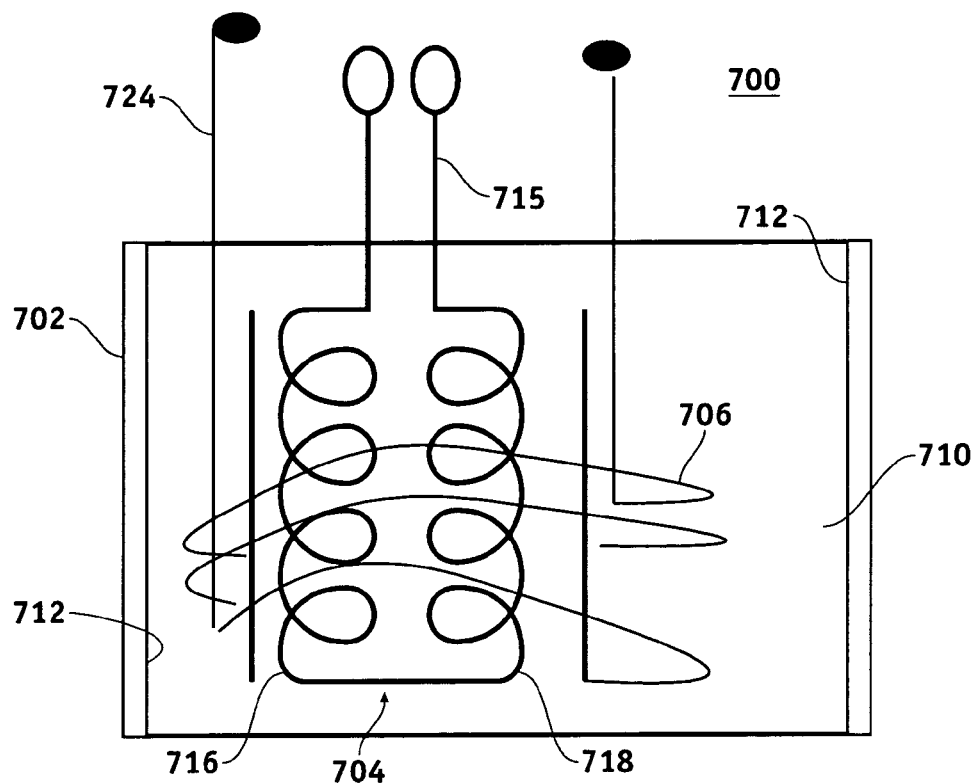
FIG. 10 is a schematic side view of a portion of a high frequency eddy current probe configured in accordance with an example embodiment of the invention.
Figure 11:
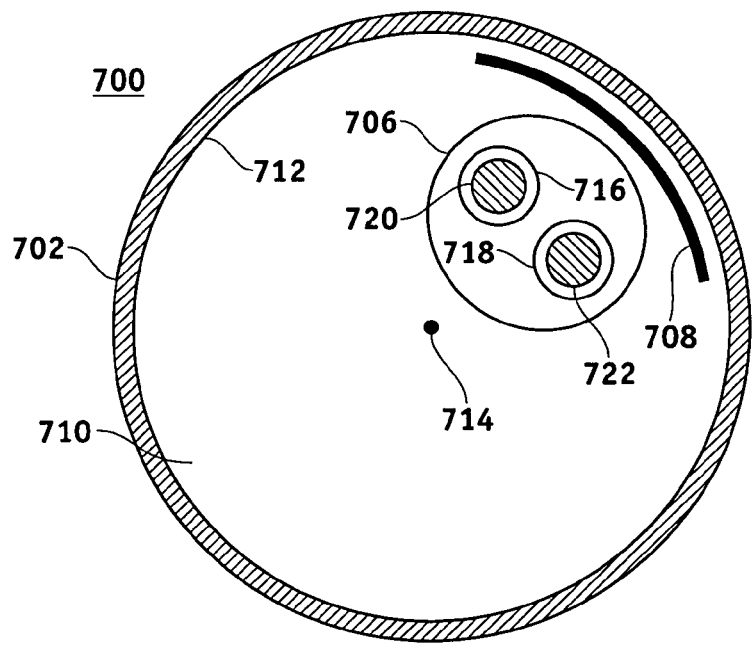
FIG. 11 is a schematic cross sectional view of a high frequency eddy current probe configured in accordance with an example embodiment of the invention, as viewed from line A-A in FIG. 9.

FIG. 10 is a schematic side view of a portion of a high frequency eddy current probe 700 configured in accordance with an example embodiment of the invention, and FIG. 11 is a schematic cross sectional view of probe 700, as viewed from line A-A in FIG. 9. Probe 700 generally includes a probe tip housing 702, a differential sensing coil arrangement 704, a reflection coil 706, and a partial electromagnetic shield 708. Probe tip housing 702, which is formed from a nonconductive material such as plastic, includes an interior 710, a perimeter 712, and a rotating axis 714. In this example, probe tip housing 702 is cylindrical in shape and rotating axis 714 represents the center and longitudinal axis of the cylinder.

Differential sensing coil arrangement 704 is located within interior 710 of probe tip housing 702 in a position that is offset from rotating axis 714 and biased toward perimeter 712 of probe tip housing 702 (see FIG. 11). The offset orientation of differential sensing coil arrangement 704 results in a constant scan rate if probe 700 is rotated at a fixed speed. In the practical embodiment of the invention, differential sensing coil arrangement 704 includes a plurality of sensing coils wound in opposition. In this regard, differential sensing coil arrangement 704 may be formed from a single conductive wire 715. For example, conductive wire 715 may be an insulated copper wire that forms a number of consecutive wraps or loops to create inductive coils.

In particular, differential sensing coil arrangement 704 includes a first sensing coil 716 and a second sensing coil 718 in close proximity to each other. In the preferred embodiment, first sensing coil 716 and second sensing coil 718 are cylindrically wound, and are adjacent to each other. First sensing coil 716 and second sensing coil 718 may be wound around a respective ferromagnetic core 720, 722 (not shown in FIG. 10), e.g., a cylindrical ferrite core. As depicted in FIG. 10 and FIG. 11, first sensing coil 716, second sensing coil 718, and ferromagnetic cores 720, 722 are preferably oriented such that their longitudinal axes are approximately perpendicular to the surface under inspection. The material used for conductive wire 715, the gauge of conductive wire 715, the coil length, diameter, pitch, and number of turns of first sensing coil 716 and second sensing coil 718, and other characteristics of differential sensing coil arrangement 704 may be selected to suit the requirements of the particular application.

Reflection coil 706 is wound around differential sensing coil arrangement 704. In practice, reflection coil 706 is insulated from first sensing coil 716 and second sensing coil 718 of differential sensing coil arrangement 704. Reflection coil 706 may be formed from a single conductive wire 724 wound in a substantially cylindrical shape around differential sensing coil arrangement 704. Conductive wire 724 may be an insulated copper wire that forms a number of consecutive wraps or loops to create an inductive coil. Reflection coil 706 is preferably oriented such that its longitudinal axis is approximately perpendicular to the surface under inspection. The material used for conductive wire 724, the gauge of conductive wire 724, the coil length, diameter, pitch, and number of turns of reflection coil 706, and other characteristics of reflection coil 706 may be selected to suit the requirements of the particular application.

Partial electromagnetic shield 708 is depicted in FIG. 11. Shield 708 may be formed from any suitable electromagnetic shielding material, such as a high permeability metal, or a μ-metal material. Suitable shield materials include, without limitation, steel and ferrite. Shield 708 is coupled to probe tip housing 702 and it is positioned such that differential sensing coil arrangement 704 is located between shield 708 and rotating axis 714. More specifically, shield 708 is positioned within interior 710 of probe tip housing 702 and between differential sensing coil arrangement 704 and perimeter 712 of probe tip housing 702. In the preferred embodiment, shield 708 is positioned within interior 710 and between reflection coil 706 and perimeter 712. These respective positions and orientations are shown in FIG. 11. This preferred arrangement protects differential sensing coil arrangement 704 and reflection coil 706 from unwanted interference originating outside probe tip housing 702.

In the example embodiment of the invention, partial electromagnetic shield 708 spans only a portion of perimeter 712 of probe tip housing 702 (see FIG. 11). In practice, shield 708 spans only that portion of perimeter 712 that is proximate reflection coil 706 and differential sensing coil arrangement 704. In other words, shield 708 does not completely surround reflection coil 706, differential sensing coil arrangement 704, or probe tip housing 702. In the example embodiment, shield 708 is large enough to eclipse, cover, or "hide" reflection coil 706 and differential sensing coil arrangement 704 from electromagnetic interference. In this regard, shield 708 is depicted as an arc that spans at least the sector of perimeter 710 upon which reflection coil 706 would be projected. The partial nature of shield 708 is desirable to ensure that high frequency eddy current probe 700 interrogates the space generally defined by interior 710 of probe tip housing 702 and disregards the edge of the lap joint when sensing coil arrangement 704 has rotated near the lap joint.

Figure 13:
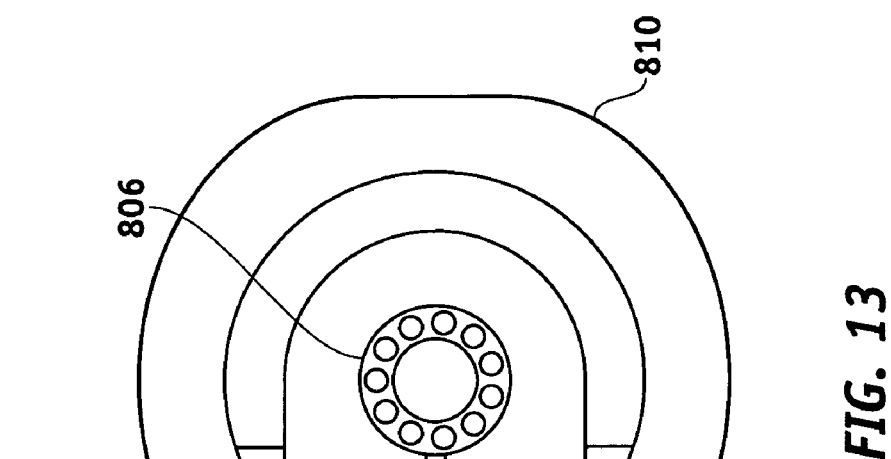
FIG. 13 is an end view of the rotary mount shown in FIG. 12, as viewed from line B-B.
Figure 12:
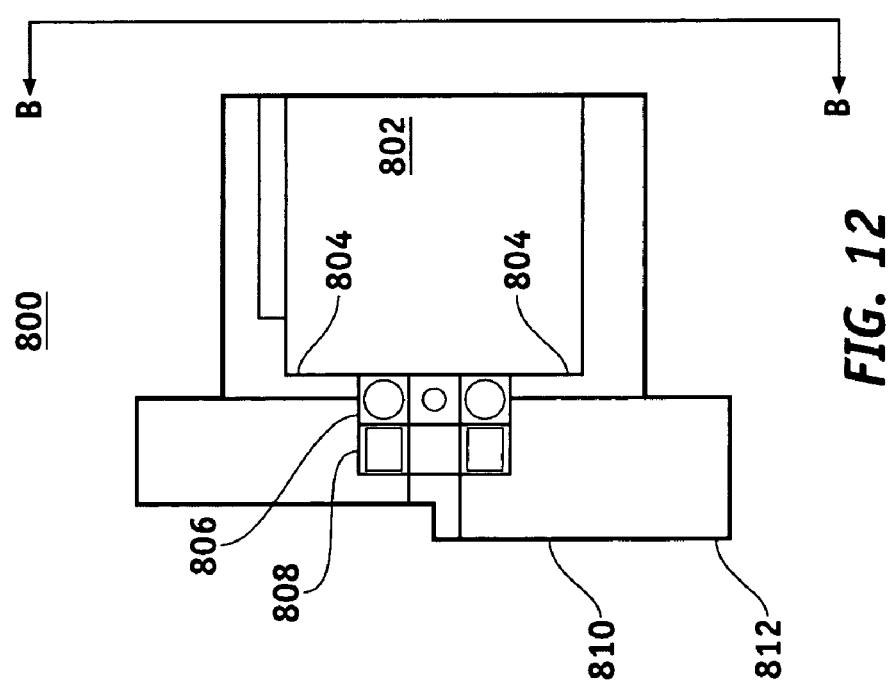
FIG. 12 is a longitudinal cross sectional view of an eddy current probe rotary mount configured in accordance with an example embodiment of the invention.
Figure 15:
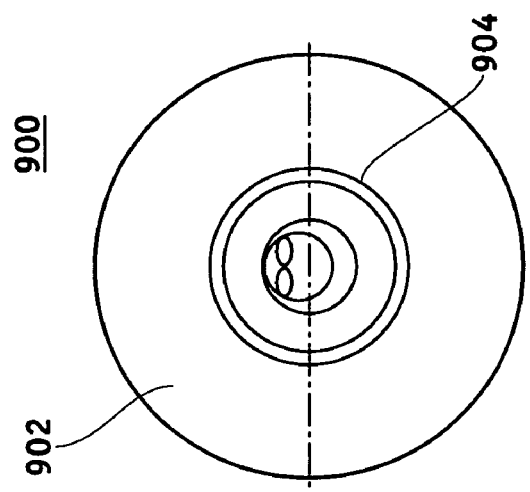
FIG. 15 is an end view of the rotary eddy current probe shown in FIG. 14, as viewed from line C-C.
Figure 14:
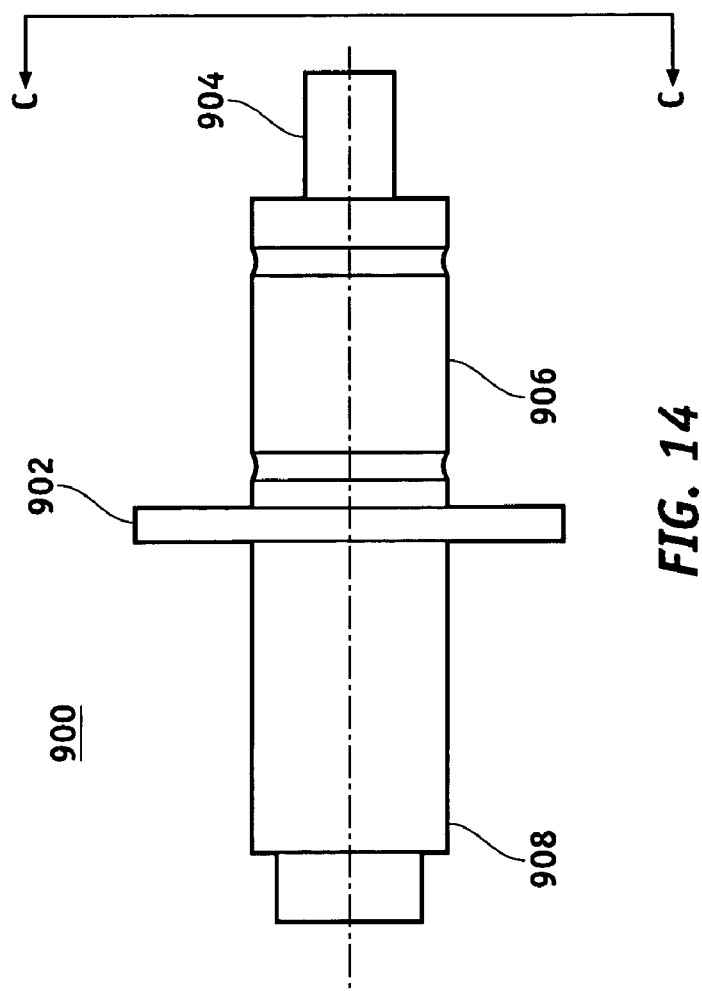
FIG. 14 is a side view of a rotary eddy current probe configured in accordance with an example embodiment of the invention.

FIG. 12 is a longitudinal cross sectional view of a rotary mount 800 configured in accordance with an example embodiment of the invention, and FIG. 13 is an end view of rotary mount 800 as viewed from line B-B in FIG. 12. FIG. 14 is a side view of a rotary eddy current probe 900 configured in accordance with an example embodiment of the invention, and FIG. 15 is an end view of rotary eddy current probe 900, as viewed from line C-C in FIG. 14. As mentioned above, rotary mount 800 is preferably designed to provide a stable platform for probe 900 that allows probe 900 to rotate at speeds of up to 3000 RPM during eddy current testing of a test part.

Rotary mount 800 includes a cavity 802 that receives probe 900. In particular, the diameter of cavity 802 is sized to accommodate a flange 902 of probe 900. When assembled, flange 902 rests upon a mounting surface 804 defined by cavity 802. Rotary mount 800 may also include a ball bearing assembly 806 and a roller bearing assembly 808 coupled in a coaxial orientation within a base 810 of rotary mount 800. These bearing assemblies may be coupled within rotary mount 800 such that their outer races are fixed, thus allowing their inner races to freely rotate.

Rotary eddy current probe 900 preferably includes a probe tip housing 904 (as described above) and a bearing engagement section 906. When probe 900 is coupled to rotary mount 800, probe tip housing 904 extends beyond the inner races of the bearing assemblies and is positioned at a desired height above the contact surface of base 810. Bearing engagement section 906, however, is dimensioned for coupling with the inner races of the bearing assemblies, thus facilitating smooth and wobble-free rotation of probe 900 within rotary mount 800. Probe 900 may also include a drive section 908 that is coupled to the rotary drive motor as described above.

In accordance with one example embodiment, probe tip housing 904 is approximately 0.188 inch in diameter, and extends approximately 0.157 inch from the end of bearing engagement section 906. In addition, bearing engagement section 906 is approximately 0.314 inch in diameter, which provides for a light press fit engagement with the inner races of the bearing assemblies (the diameters of the inner races may be approximately 0.314 inch, and the diameters of the outer races may be approximately 0.870 inch). In this embodiment, the diameter of flange 902 is approximately 0.437 inch, the depth of cavity 802 is approximately 1.745 inch, and the thickness of base 810 measured from mounting surface 804 to a contact surface 812 is approximately 0.700 inch. It should be appreciated that these dimensions correspond to one example embodiment, and that the dimensions can vary to suit the requirements of the given application.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

What is claimed is:

1. A high frequency rotary eddy current probe comprising:
a probe tip housing having an interior, a perimeter housing wall, and a rotating axis;
a differential sensing coil arrangement comprising a group of sensing coils located within said interior in a position such that the group is offset from said rotating axis and biased toward said perimeter housing wall; and
a partial electromagnetic shield coupled to said probe tip housing and positioned such that said differential sensing coil arrangement is located between said partial electromagnetic shield and said rotating axis, wherein a cross section of said partial electromagnetic shield in a plane perpendicular to said rotating axis spans only a portion of said perimeter housing wall.

2. A high frequency rotary eddy current probe according to claim 1, said partial electromagnetic shield being positioned within said interior and between said differential sensing coil arrangement and said perimeter housing wall of said probe tip housing.

3. A high frequency rotary eddy current probe according to claim 1, said differential sensing coil arrangement comprising a plurality of sensing coils wound in opposition.

4. A high frequency rotary eddy current probe according to claim 3, further comprising a plurality of ferromagnetic cores, each of said plurality of sensing coils being wound around one of said ferromagnetic cores.

5. A high frequency rotary eddy current probe according to claim 4, each of said plurality of ferromagnetic cores being cylindrical in shape.

6. A high frequency rotary eddy current probe according to claim 3, said plurality of sensing coils being adjacent to each other.

7. A high frequency rotary eddy current probe according to claim 1, further comprising a reflection coil wound around said differential sensing coil arrangement, said reflection coil being insulated from said differential sensing coil arrangement.

8. A high frequency rotary eddy current probe according to claim 7, said partial electromagnetic shield being positioned within said interior and between said reflection coil and said perimeter housing wall of said probe tip housing.

9. A high frequency rotary eddy current probe according to claim 1, said partial electromagnetic shield comprising a μ-metal material.

10. An eddy current crack detection device comprising:
a rotary drive;
a high frequency rotary eddy current probe coupled to said rotary drive, said high frequency rotary eddy current probe comprising:
a probe tip housing having an interior, a perimeter housing wall, and a rotating axis;

a differential sensing coil arrangement comprising a group of sensing coils located within said interior in a position such that the group is offset from said rotating axis and biased toward said perimeter housing wall; and a partial electromagnetic shield coupled to said probe tip housing and positioned such that said differential sensing coil arrangement is located between said partial electromagnetic shield and said rotating axis, wherein a cross section of said partial electromagnetic shield in a plane perpendicular to said rotating axis forms an arc that spans only a portion of said perimeter housing wall; and a rotary mount coupled to said rotary drive and to said high frequency rotary eddy current probe, said rotary mount being configured to stabilize said probe tip housing while said rotary drive rotates said high frequency rotary eddy current probe.

11. An eddy current crack detection device according to claim 10, said partial electromagnetic shield being positioned within said interior and between said differential sensing coil arrangement and said perimeter housing wall of said probe tip housing.

12. An eddy current crack detection device according to claim 10, said differential sensing coil arrangement comprising two adjacent cylindrical sensing coils wound in opposition.

13. An eddy current crack detection device according to claim 12, further comprising a plurality of ferromagnetic cores, each of said two adjacent cylindrical sensing coils being wound around one of said ferromagnetic cores.

14. An eddy current crack detection device according to claim 10, further comprising a reflection coil wound around said differential sensing coil arrangement, said reflection coil being insulated from said differential sensing coil arrangement.

15. An eddy current crack detection device according to claim 14, said partial electromagnetic shield being positioned within said interior and between said reflection coil and said perimeter housing wall of said probe tip housing.

16. An eddy current crack detection device according to claim 14, further comprising a test signal connector coupled to said reflection coil, said test signal connector being configured to provide an alternating current test signal to said reflection coil, said alternating current test signal having a frequency between 100 kHz and 3.0 MHz.

17. An eddy current crack detection device according to claim 10, said rotary drive being configured to rotate said high frequency rotary eddy current probe between 100 and 3000 RPM.

18. A high frequency rotary eddy current probe comprising:

a probe tip housing having an interior, a perimeter housing wall, and a rotating axis;

a differential sensing coils arrangement, of only two sensing coils, located within said interior in a position offset from said rotating axis;

a reflection coil wound around said differential sensing coil arrangement, said reflection coil being positioned off-axis relative to said rotating axis; and a partial electromagnetic shield located within said interior and between said reflection coil and said perimeter housing wall of said probe tip housing, wherein a cross section of said partial electromagnetic shield in a plane perpendicular to said rotating axis spans at least a sector of said perimeter housing wall upon which said reflection coil would be projected, without completely surrounding said differential sensing coils arrangement.

19. A high frequency rotary eddy current probe according to claim 18, said differential sensing coils arrangement comprising two cylindrical sensing coils wound in opposition.

20. A high frequency rotary eddy current probe according to claim 19, further comprising a plurality of cylindrical ferromagnetic cores, each of said two cylindrical sensing coils being wound around one of said cylindrical ferromagnetic cores.

21. A high frequency rotary eddy current probe according to claim 18, said two sensing coils being adjacent to each other.

* * * * *